United States Patent [19]

Hirai et al.

[11] 4,054,586

[45] Oct. 18, 1977

[54] PROCESS FOR PREPARING 1-AMINOANTHRAQUINONE HAVING HIGH PURITY

[75] Inventors: Yutaka Hirai; Katsuharu Miyata; Tagui Osawa, all of Ohmuta, Japan

[73] Assignee: Mitsui Toatsu Chemicals Incorporated, Tokyo, Japan

[21] Appl. No.: 641,284

[22] Filed: Dec. 16, 1975

[30] Foreign Application Priority Data

Dec. 20, 1974 Japan .................. 49-145612
Dec. 20, 1974 Japan .................. 49-145613

[51] Int. Cl.$^2$ .................................................. C09B 1/16
[52] U.S. Cl. ...................................................... 260/378
[58] Field of Search ......................................... 260/378

[56] References Cited

U.S. PATENT DOCUMENTS

| 2,738,354 | 3/1956 | Kern et al. ............... 260/378 X |
| 3,907,838 | 9/1975 | Thiem et al. ............. 260/378 |
| 3,931,253 | 6/1976 | Krenmueller et al. ..... 260/378 |

Primary Examiner—Paul F. Shaver
Attorney, Agent, or Firm—Sherman & Shalloway

[57] ABSTRACT

A process for preparing 1-aminoanthraquinone having high purity, which comprises either 1. hydrogenating 1-nitroanthraquinone in an aqueous medium in the presence of a base using a hydrogenating catalyst, and then oxidizing the hydrogenation product, or 2. hydrogenating crude 1-nitroanthraquinone containing dinitroanthraquinones as impurities or crude 1-aminoanthraquinone containing diaminoanthraquinones as impurities in an aqueous medium in the presence of a base using a hydrogenating catalyst, stopping the hydrogenation at a time when the 1-nitroanthraquinone or 1-aminoanthraquinone has been substantially reduced to 1-aminoanthrahydroquinone but the dinitroanthraquinones or diaminoanthraquinones remain substantially unreduced to diaminoanthrahydroquinones, removing water-insoluble materials from the reaction mixture, and then oxidizing the remaining water-soluble residue.

14 Claims, No Drawings

PROCESS FOR PREPARING 1-AMINOANTHRAQUINONE HAVING HIGH PURITY

This invention relates to a process for preparing 1-aminoanthraquinone having high purity, and more specifically, to a process for preparing high purity 1-aminoanthraquinone from pure 1-nitroanthraquinone, crude 1-nitroanthraquinone or crude 1-aminoanthraquinone.

1-Aminoanthraquinone is an important intermediate for anthraquinonic disperse dyes, vat dyes or pigments, and has previously been prepared through anthraquinone-1-sulfonic acid which can be obtained by sulfonating anthraquinone. However, since a mercury catalyst is used in the sulfonation process, it has become difficult to perform this process in view of its adverse effects on the working environment and the control of environmental pollution. Various methods for preparing 1-aminoanthraquinone which can replace the conventional process have been investigated, and one of such methods comprises nitrating anthraquinone to form 1-nitroanthraquinone, and reducing it with an alkali sulfide to form 1-aminoanthraquinone.

Generally, nitro compounds are reduced effectively by catalytic hydrogenation, and this technique has gained wide commercial acceptance. In spite of this, catalytic hydrogenation has scarcely been utilized for the reduction of 1-nitroanthraquinone, and the only pertinent literature reference known is V. M. Chursina, Izv. Akad. Nauk. SSSR, Ser. Khim., 1969, page 2550 which discloses the hydrogenation of 1-nitroanthraquinone in a sulfuric acid solvent using a palladium catalyst. The main reasons for this are cited below.

Since 1-nitroanthraquinone as a raw material and 1-aminoanthraquinone as a reduction product thereof are only sparingly soluble in common organic solvents, the reaction mixture becomes slurry-like, and this causes difficulties in performing the reaction. The catalyst and the reaction product are difficult to separate from each other. Furthermore, during the hydrogenation reaction, the hydrogenation of a carbonyl group on the anthraquinone nucleus and of the nucleus itself tends to occur in addition to the reduction of the nitro group. This results in the formation of various by-products such as 1-aminoanthrahydroquinone, 1-aminoanthranol, 1-amino-5,6,7,8-tetrahydroanthraquinone, and 1-amino-1,2,3,4,5,6,7,8-octahydroanthraquinone, and deteriorates the quality of the product.

Sulfuric acid is a solvent which can dissolve aminoanthraquinones relatively easily. In the Chursina's method described above in which hydrogenation is carried out using sulfuric acid, the reaction is so slow that very large quantities of catalyst are required. Also, various by-products such as 1-amino-4-hydroxyanthraquinone and 1-amino-4-hydroxyanthraquinone sulfonic acid are formed in large quantities.

We previously found that carboxylic acid amides can dissolve 1-aminoanthraquinone more easily than other solvents. However, we ascertained that when, for example, N,N-dimethyl formamide is used as a solvent in the hydrogenation of 1-nitroanthraquinone, the reaction is rapid, but because of the formation of unidentifiable substances in addition to the corresponding 1-aminoanthraquinone, the product cannot be used directly as dyes or pigments. Thus, we knew that carboxylic acid amides are unsuitable hydrogenation solvents.

Our efforts in an attempt to solve the above problem led to the discovery that by using an aqueous medium such as water or a mixture of water and an organic solvent, the nitro group or 1-nitroanthraquinone is reduced while the 1-nitroanthraquinone is in the suspended state, and 1-aminoanthraquinone of better quality with lesser amounts of impurities than in the case of using an organic solvent can be obtained. According to this method, however, when the particles of 1-nitroanthraquinone have a large size, it sometimes happens that only the surfaces of the particles are hydrogenated, but their insides remain unreacted or become a reaction intermediate. The unreacted matter and the reaction intermediate adversely affect the quality and yield of 1-aminoanthraquinone as a final product. Furthermore, since 1-aminoanthraquinone is scarcely soluble in water, it must be collected together with the catalyst, and the mixture is dissolved in a solvent such as sulfuric acid to separate the catalyst. In addition, since the resulting 1-aminoanthraquinone contains a 2-amino isomer and 1,5-, 1,8-, 1,6- and 1,7-diamino isomers ascribable to a 2-nitro isomer and 1,5-, 1,8-, 1,6- and 1,7-dinitro isomers formed as by-products in the nitration of anthraquinone, it is necessary to remove these isomers. Separation of the 1,5- and 1,8-diamino isomers is not easy, however.

We furthered our investigations in order to get over this difficulty, and finally found that 1-aminoanthraquinone of good quality can be obtained in high yields by hydrogenating 1-nitroanthraquinone in an aqueous medium using an ordinary hydrogenating catalyst in the presence of an inorganic or organic base, and oxidizing the hydrogenation product with a suitable oxidizing agent such as air or hydrogen peroxide.

Microscopically, it is believed that the following reaction occurs repeatedly in the process of this invention. On the surface of the particles of 1-nitroanthraquinone, the reduction of the 1-nitroanthraquinone occurs to form 1-aminoanthraquinone. The 1-aminoanthraquinone further undergoes hydrogenation to form 1-aminoanthrahydroquinone. The 1-aminoanthrahydroquinone forms a water-soluble salt with a base and dissolves in the aqueous medium. As a result, a new reaction site for 1-nitroanthraquinone appears on the surface of the particles. The salt of 1-aminoanthrahydroquinone reduces 1-nitroanthraquinone to 1-aminoanthraquinone, and simultaneously becomes insoluble 1-aminoanthraquinone to release a base. When the amount of the base is below the equivalent weight based on 1-nitroanthraquinone, 1-nitroanthraquinone in an equivalent weight to the base becomes 1-aminoanthrahydroquinone, and forms a salt with the base, which exists dissolved in the aqueous medium. The remaining 1-nitroanthraquinone is present as solid 1-aminoanthraquinone. When the amount of the base is above the equivalent weight based on 1-nitroanthraquinone, all of the 1-nitroanthraquinone becomes a salt of 1-aminoanthrahydroquinone and dissolves in the aqueous medium. By the oxidation of the hydrogenation product as above, the salt of 1-aminoanthrahydroquinone is easily converted to 1-aminoanthraquinone which precipitates as crystals.

According to the process of this invention, the catalytic hydrogenation proceeds by the above-mentioned series of reactions. Thus, 1-nitroanthraquinone is always exposed on the surface of the particles and participates in the reaction. This obviates the problem encountered in the catalytic hydrogenation of 1-nitroanthraquinone in an aqueous medium not containing a base in which the reaction product covers the surface of the 1-nitroanthraquinone particles and leaves their inside unreacted or only partially reacted.

The 1-nitroanthraquinone that can be used in the process of this invention may be not only pure 1-nitroanthraquinone, but also crude 1-nitroanthraquinone obtained by the nitration of anthraquinone, or 1-nitroanthraquinone roughly purified by known methods. The known roughly purifying methods include, for example, recrystallization, treatment with bisulfites, treatment with organic solvents, treatment with bases, or hydroxylation.

According to the above-mentioned principle, it will be understood that the method of this invention for preparing high-purity 1-aminoanthraquinone from crude 1-nitroanthraquinone can be applied to the production of high purity 1-aminoanthraquinone from crude 1-aminoanthraquinone. Accordingly, the present invention includes an embodiment of preparing high purity 1-aminoanthraquinone from crude 1-aminoanthraquinone in addition to an embodiment of preparing high purity 1-aminoanthraquinone from crude 1-nitroanthraquinone. In the production of high purity 1-aminoanthraquinone from crude 1-aminoanthraquinone, crude 1-aminoanthraquinone used as a starting substance can be prepared by various methods. For example, it can be prepared by reducing crude 1-nitroanthraquinone in an aqueous alkali solution with a sulfur compound such as an alkali sulfide, an alkali hydrosulfide or an alkali polysulfide, a saccharide such as glucose, a hydrazine, or a dithionite, or in an acidic aqueous solution with sulfur dioxide or a metal such as iron, aluminum, zinc or copper, or by hydrogenating the crude 1-nitroanthraquinone in an organic solvent or an aqueous medium using a hydrogenation catalyst. It can be obtained also by treating crude 1-nitroanthraquinone with ammonia in a solvent to substitute the nitro group by an amino group. Another method involves reacting crude anthraquinone-1-sulfonic acid with ammonia at a elevated pressure. The crude 1-aminoanthraquinone can be used in the process of this invention either after isolation or without isolation.

Thus, according to this invention, there is provided a process for preparing 1-aminoanthraquinone of high purity, which comprises (1-hydrogenating 1-nitroanthraquinone in an aqueous medium in the presence of a base using a hydrogenating catalyst, and then oxidizing the hydrogenation product, or (2) hydrogenating crude 1-nitroanthraquinone containing dinitroanthraquinones as impurities, or crude 1-aminoanthraquinone containing diaminoanthraquinones as impurities in an aqueous medium in the presence of a base using a hydrogenating catalyst, stopping the hydrogenation at a time when the 1-nitroanthraquinone or 1-aminoanthraquinone has been substantially reduced to 1-aminoanthrahydroquinone but the dinitroanthraquinones or diaminoanthraquinones remain substantially unreduced to diaminopanthrahydroquinones, removing water-insoluble materials from the reaction mixture, and then oxidizing the remaining water-soluble residue.

The hydrogenation in accordance with the process of this invention can be performed by customary methods at normal atmospheric pressure or at an elevated pressure. For example, according to the atmospheric pressure method, a reactor equipped with a stirrer and a hydrogen-introducing tube is charged with the starting material, anaqueous medium, an organic or inorganic base, and a catalyst, and the reaction is carried out with stirring at a predetermined temperature while introducing hydrogen. According to the elevated pressure method, these materials are placed in a pressure reactor, and reacted with stirring or shaking while introducing hydrogen under pressure. A continuous reaction process can also be utilized in the present invention.

When water is used as the aqueous medium, the amount of water is 5 to 200 times, preferably 10 to 60 times, the weight of the starting 1-nitroanthraquinone.

An organic solvent can be used conjointly with water. The organic solvent should be inert to the reaction system, and its examples include aromatic hydrocarbons whose aromatic nucleus is substituted by one to several halogen atoms, aliphatic, araliphatic and cycloaliphatic hydrocarbons containing 5 to 12 carbon atoms, halogenated aliphatic hydrocarbons containing 1 to 6 carbon atoms and substituted by one to several halogen atoms, ethers such as anisole, dialkyl ethers, tetrahydrofuran or dioxane, aliphatic and cycloaliphatic ketones such as acetone, methyl ethyl ketone or cyclohexanone, and mono- or polyhydric aliphatic and cycloaliphatic alcohols containing 1 to 6 carbon atoms.

When the organic solvent is conjointly used, it may be added before or during the hydrogenation reaction. When the organic solvent is conjointly used, the post-treatment of the product (the removal of insoluble materials and the oxidation of soluble materials) subsequent to the hydrogenation reaction can be performed either after recovering the organic solvent or without recovering it.

The amount of the organic solvent that can be used is up to 50 times, preferably up to 20 times, the weight of the starting 1-nitroanthraquinone or 1-aminoanthraquinone. The organic solvent is mixed with water in the above-mentioned amount to form the aqueous medium. The proportion of the organic solvent in the aqueous medium is generally not more than 40% by weight, preferably not more than 30% by weight.

The conjoint use of the organic solvent changes the properties of the interface between the reaction medium and the suspended materials, and brings about favorable results for the reaction. For example, the reaction can be carried out while maintaining the concentration of the slurry high, or the rate of reaction is somewhat increased. Even when the starting 1-nitroanthraquinone or 1-aminoanthraquinone contains an organic solvent entrained from its manufacturing process, it is not necessary to remove it prior to use in the process of this invention. However, the reaction can usually be performed using only water as a reaction medium, and it is not necessary to add an organic solvent.

In the process of this invention, a surface active agent that does not adversely affect the hydrogenation reaction can also be used. Examples of suitable surface active agents are nonionic surface active agents such as polyoxyethylene alkyl ethers or polyoxyethylene alkylaryl ethers, and anionic surface active agents such as alkylarylsulfonic acids. The amount of the surface active agent that can be used in this invention is 0.001 to 1.0 time, preferably 0.005 to 0.5 time, the weight of the starting 1-nitroanthraquinone or 1-aminoanthraquinone.

The addition of a surface active agent changes the properties of the interface between the reaction medium and the suspended materials, and therefore, brings about favorable results for the reaction. For example, the reaction can be carried out while maintaining the concentration of the slurry high, and the reaction mixture can be stirred easily. Furthermore, the rate of reaction is somewhat increased. Generally, however, the reaction can be carried out satisfactorily even without using surface active agents.

The inorganic and organic bases used in this invention may be those which are usually employed. Examples of particularly suitable bases are hydroxides, oxides, carbonates, acetates and phosphates of alkali metals or alkaline earth metals such as sodium, potassium, calcium, barium and magnesium, ammonia, diethylamine, morpholine, piperidine, ethanolamine, piperazine, ethylenediamine, 1,4-diazabicyclooctane, and 1,7-diazaundecene. These bases can be used either alone or as mixtures. The amount of the base is at least 1 mole, preferably 1 to 20 moles, per mole of the starting 1-nitroanthraquinone or 1-aminoanthraquinone. Preferably, these bases are added at the ouset of the hydrogenation reaction, but a part or the whole of it may be added during the reaction.

The hydrogenating catalyst used in the process of this invention may be any hydrogenating catalyst usually employed for converting nitro compounds to amino compounds by catalytic hydrogenation. Examples include catalysts containing a metal such as palladium, platinum, ruthenium, rhodium, nickel, cobalt or copper as an active ingredient. Palladium catalysts supported on a carrier such as carbon, alumina, diatomaceous earth, or silica gel are especially suitable. The amount of the catalyst differs according to the reaction conditions and the type of the catalyst. But when the reaction is carried out using a supported palladium catalyst, the suitable amount of the catalyst is 0.01 to 1.0 part by weight, as palladium metal, per 100 parts by weight of the starting material. When the catalyst is used without a carrier, for example, in the case of palladium black, the suitable amount of the catalyst is 0.01 to 5.0 parts by weight per 100 parts by weight of the starting material.

The reaction temperature that can be used in this invention is 0° to 160° C., preferably 10° to 80° C., more preferably 15° to 60° C., and the reaction pressure is preferably from atmospheric pressure to 100 Kg/cm$^2$. The reaction in accordance with this invention, however, proceeds even at room temperature and atmospheric pressure. When the reaction temperature is too high, undesirable by-products are liable to be formed.

After the end of the hydrogenation reaction in accordance with the process of this invention, the whole is or at least a part, of 1-nitroanthraquinone or 1-aminoanthraquinone is reduced to 1-aminoanthrahydroquinone. An oxidizing agent is added to the reaction mixture after the hydrogenation to oxidize the reaction product. Examples of the oxidizing agent that can be used in this invention are air, oxygen, hydrogen, peroxide, sodium peroxide, perborates, peroxides or organic acids or salts thereof, peroxides or organic acid anhydrides persulfates, hypochlorites, bleaching powder, and chlorine. Of these, air is especially preferred. For example, by passing air into the reaction mixture at a temperature of 0° to 120° C., preferably 10° to 80° C., the reacton product can be oxidized. The time required for the oxidation is 0.5 to 5 hours under preferred conditions, and less than 0.5 hour under more preferred conditions.

The end point of the oxidation reaction can be detected by the absence of a yellow oozed part ascribable to 1-aminoanthrahydroquinone when the reaction mixture is dropped on a filter paper.

The 1-aminoanthraquinone formed by the oxidation of 1-aminoanthrahydroquinone is precipitated from the aqueous medium. The reaction product is filtered and a mixture of the catalyst and the resulting 1-aminoanthraquinone is collected. The 1-aminoanthraquinone is separated from this mixture using a solvent that can easily dissolve 1-aminoanthraquinone. Examples of suitable solvents for this purpose include aliphatic glycols such as ethylene glycol, propylene glycol, diethylene glycol and dipropylene glycol; alicyclic alcohols such as cyclohexanol and methyl cyclohexanol; carboxylic acid amides such as N,N-dimethyl formamide, N,N-dimethyl acetamide and N-methyl-2-pyrrolidone; ethers such as dioxane, tetrahydrofuran and methoxybenzene; substituted aromatic hydrocarbons such as toluene, xylene, chlorobenzene and dichlorobenzene; ether alcohols such as methoxyethanol; sulfuric acid; and dimethyl sulfoxide. The 1-aminoanthraquinone solution separated from the catalyst is either cooled, diluted with a solvent which sparingly dissolves 1-aminoanthraquinone (such as water), or concentrated, thereby to recover the 1-aminoanthraquinone efficiently.

When the hydrogenation is carried out using an alkali metal or alkaline earth metal hydroxide, such as sodium hydroxide or potassium hydroxide, as the base in an amount of at least $2/n$ (n being the atomic valency of the alkali metal or alkaline earth metal) moles per mole of the starting 1-nitroanthraquinone of 1-aminoanthraquinone, all the 1-nitroanthraquinone dissolves as a salt of 1-aminoanthrahydroquinone. Accordingly, the catalyst can be separated without using an organic solvent. Separation of the catalyst can usually be effected in an atmosphere of air, but preferably in an atmosphere of an inert gas such as nitrogen. By oxidizing the filtrate left after the separation of the catalyst, 1-aminoanthraquinone can be obtained with good efficiency.

In order to obtain high purity 1-aminoanthraquinone with good efficiency, the difference between the rate of reduction of 1-aminoanthraquinone to its hydroquinone derivative and the rate of reduction of diaminoanthraquinones to their hydroquinone derivatives is utilized in this invention. When 1-nitroanthraquinone containing dinitroanthraquinones such as 1,5-, 1,8-, 1,6- and 1,7-dinitroanthraquinone formed as a by-product of the nitration of anthraquinone is hydrogenated by the above-mentioned method, the reduction of the nitrogroup first takes place, then the reduction of 1-aminoanthraquinone to its hydroquinone derivatives, and finally, the reduction of diaminoanthraquinone to its hydroquinone derivative proceeds. Similar reactions take place when crude 1-aminoanthraquinone is used as the starting material. The rate of reduction of 1-aminoanthraquinone to its hydroquinone derivative is faster than the rate of reduction of diaminoanthraquinones to its hydroquinone derivative.

Thus, when, for example, 1-nitroanthraquinone containing ordinary amounts of 1,5-dinitroanthraquinone is to be hydrogenated, the time at which hydrogen has been absorbed in an amount equal to the sum of the amount of hydrogen required to convert 1-nitroanthraquinone to 1-aminoanthrahydroquinone and the amount of hydrogen required to convert 1,5-dinitroanthraquinone to 1,5-diaminoanthraquinone can be regarded as the end point of the hydrogenation reaction. When the content of 1,5-dinitroanthraquinone in 1-nitroanthraquinone is as high as, say, 20% by weight, the time at which hydrogen has been absorbed in an amount of 90% of the theoretical amount required to reduce all 1-aminoanthraquinone to 1-aminoanthrahydroquinone after absorbing hydrogen in an amount required to reduce all the nitro group to an amino group can be regarded as the end point of hydrogenation. When the content of 1,5-dinitroanthraquinone in 1-nitroanthraquinone is as low as, say, 2% by weight, the time at which hydrogen has been absorbed in an amount of 98 to 101% of the theoretical amount can be regarded as the end point of hydrogenation.

Furthermore, when, for example, 1-aminoanthraquinone containing ordinary amounts of 1,5-diaminoanthraquinone is to be hydrogenated, the time at which hydrogen has been abosrbed in an amount required to convert 1-aminoanthraquinone to 1-aminoanthrahydroquinone can be regarded as the end point of hydrogenation. When the content of 1,5-diaminoanthraquinone in crude 1-aminoanthraquinone is as high as, say, 20% by weight, the time at which hydrogen has been absorbed in an amount corresponding to 90% of the theoretical amount required to reduce 1-aminoanthraquinone completely to 1-aminoanthrahydroquinone can be regarded as the end point of hydrogenation. When the content of 1,5-diaminoanthraquinone in crude 1-aminoanthraquinone is as low as, say, 2% by weight, the time at which hydrogen has been absorbed in an amount corresponding to 90 to 101% of the theoretical amount can be regarded as the end point of hydrogenation.

In an actual reaction operation, the amount of hydrogen absorbed can be easily controlled by measuring the amount of hydrogen absorbed or observing changes in the rate of hydrogen absorption, or by a polarographic analysis.

According to the present invention, diamino isomers can be efficiently removed on the basis of the knowledge of the dinitro isomers or diamino isomers content of the starting crude 1-nitroanthraquinone or crude 1-aminoanthraquinone, and high purity 1-aminoanthraquinone can be easily obtained.

The process of this invention can be applied to 1-nitroanthraquinone or 1-aminoanthraquinone containing less than 50% by weight, especially less than 25% by weight, of dinitro isomers or diamino isomers respectively.

According to the process of this invention, 1-aminoanthraquinone having a diamino isomer content of less than 2% by weight and a purity of at least 97% by weight, and under preferred conditions, having a diamino isomer content of less than 1% by weight and purity of at least 99% by weight can generally be obtained.

The following Examples specifically illustrate the present invention.

EXAMPLE 1

A 1-liter electromagnetically stirred cylindrical glass reactor was charged with 2.53 g (0.01 mole) of 1-nitroanthraquinone (roughly purified product with no impurity detected by thin-layer chromatography), 52.0 g (0.013 mole as sodium hydroxide) of a 1% aqueous solution of sodium hydroxide and 0.051 g of 5% palladium-carbon. The inside of the reactor was purged with hydrogen, and the 1-nitroanthraquinone was hydrogenated with stirring at room temperature. In 3 hours when 0.035 mole of hydrogen was absorbed, the hydrogen inside the reactor was replaced by nitrogen and then by air. The mixture was stirred at 20° to 30° C. for 30 minutes to oxidize the perhydrogenated product.

The reaction product was separated by filtration, and 15 g of N,N-dimethyl formamide was added. The mixture was stirred and then filtered, and 150 g of water was added to the filtrate to obtain 2.05 g (yield 92% of theory) of 1-aminoanthraquinone. The product was analyzed by infrared absorption spectroscopy, and found to have a purity of 98% by weight. No absorption ascribable to by-products was observed.

When the above procedure was repeated using a 30% aqueous solution of hydrogen peroxide, a 15% aqueous solution of sodium hypochlorite, or sodium perborate instead of the air in the oxidation treatment, the same results were obtained.

EXAMPLE 2

A 160 ml. electromagnetically stirred autoclave was charged with 2.53 g (0.01 mole) of 1-nitroanthraquinone (roughly purified product with no impurity detected by thin-layer chromatography), 52 g (0.05 mole) of a 4% aqueous solution of sodium hydroxide and 0.07 g of Raney nickel. The 1-nitroanthraquinone was hydrogenated with stirring at room temperature and a pressure of 6 to 3 Kg/cm$^2$·G. The reaction proceeded smoothly, and stopped in 6 hours with the absorption of 0.04 mole of hydrogen. The inside of the autoclave was purged with nitrogen, and the reaction mixture was filtered in an atmosphere of nitrogen to separate the catalyst. The filtrate was oxidized with air at 20° to 30°C. for 1 hour with stirring to afford 2.1 g of 1-aminoanthraquinone having a purity of 97% by weight in a yield of 94% of theory. By a thin layer chromatographic analysis, no impurity was detected in the resulting product.

EXAMPLE 3

The same hydrogenation reaction as in Example 1 was carried out except that 1.0 g (0.01 mole) of morpholine and 52 g of water were used instead of the 1% aqueous solution of sodium hydroxide. The reaction mixture was oxidized with air at 20° to 30°C. for 30 minutes, and the reaction product was recovered together with the catalyst from the reaction mixture. The mixture of the product and the catalyst was dissolved in N,N-dimethyl formamide, and the catalyst was separated by filtration. The filtrate was diluted with water, and the crystals precipitated were collected, washed with water, and dried to afford 2.1 g of 1-aminoanthraquinone having a purity of 98% by weight in a yield of 94% of theory. No impurity was detected by a thin-layer chromatographic analysis.

When the above procedure was repeated using 2.0 g (0.01 mole) of triethanolamine of 1.0 g (0.01 mole) of piperazine instead of the morpholine, the same results were obtained.

EXAMPLE 4

A 1-liter electromagnetically stirred glass reactor was charged with 2.53 g (0.01 mole) of 1-nitroanthraquinone (roughly purified product with no impurity detected by thin-layer chromatography), 52 g of water and 0.051 g of 5% palladium-carbon. The inside of the reactor was purged with nitrogen, and with stirring at room temperature, the 1-nitroanthraquinone was hydrogenated. In 4.5 hours when 0.03 mole of hydrogen was absorbed, the hydrogen inside the reactor was replaced by nitrogen, and 2.1 g (0.052 mole) of sodium hydroxide was added. The inside of the reactor was purged with hydrogen, and the hydrogenation was continued at room temperature. In 1 hour, the absorption of hydrogen was stopped. The amount of hydrogen absorbed until then was 0.01 mole. The reaction mixture completely dissolved. The inside of the reactor was purged with nitrogen, and the reaction mixture was filtered in an atmosphere of nitrogen to separate the catalyst. The filtrate was oxidized with air at 20° to 30° C. for 2 hours with stirring to afford 2.08 g of 1-aminoanthraquinone having a purity of 98% by weight in a yield of 93% of theory. By a thin-layer chromatographic analysis, no impurity was detected.

EXAMPLE 5

A 500 ml. electromagnetically stirred flask was charged with 5.0 g of crude 1-nitroanthraquinone having a purity of 97% and containing 2% of 1,5-dinitroanthraquinone and 1% of 1,8-dinitroanthraquinone as impurities (0.0192 mole of 1-nitroanthraquinone, and 0.005 mole of all the dinitroanthraquinones), 100 g (0.1 mole) of a 4% aqueous solution of sodium hydroxide and 0.1 g of 5% palladium-carbon. The inside of the flask was purged with hydrogen, and at a reaction temperature of 30° C., they were stirred. In 3 hours, the reaction was stopped with the absorption of 0.08 mole of hydrogen. The amount of hydrogen absorbed was slightly in excess of the sum of the amount of hydrogen required to convert the nitro group to an amino group (0.0606 mole) and the amount of hydrogen required to convert 1-aminoanthraquinone to its hydroquinone derivative (0.0192 mole). The inside of the flask was purged with nitrogen, and the reaction mixture was filtered in an atmosphere of nitrogen to separate the catalyst. The filtrate was oxidized with air at 20° to 30° C. for 2 hours with stirring to afford 4.2 g of 1-aminoanthraquinone in a yield of 97.4% of theory. The product had a purity of 99% as determined by infrared absorption spectroscopy.

EXAMPLE 6

5.0 g of crude 1-nitroanthraquinone containing dinitroanthraquinones having a purity of 81% and containing 8% of 1,5-dinitroanthraquinone, 4% of 1,8-dinitroanthraquinone and 7% of other dinitroanthraquinones and being free from anthraquinone and 2-nitroanthraquinone (0.016 mole of 1-nitroanthraquinone and 0.0032 mold of all the dinitroanthraquinones) was hydrogenated in the same way as in Example 5. The reaction was stopped when the amount of hydrogen absorbed reached 0.0816 mole, and the inside of the flask was purged with nitrogen. The amount of hydrogen absorbed corresponded to the sum of the amount of hydrogen required to convert the nitro group to an amino group (0.0672 mole) and 90% of the amount of hydrogen required to convert 1-aminoanthraquinone to its hydroquinone derivative (0.0144 mole). The reaction mixture was filtered in a stream of nitrogen to separate the catalyst and insoluble materials from it. The filtrate was oxidized with air at 20° to 30° C. for 2 hours with stirring to afford 3.2 g of 1-aminoanthraquinone having a purity of 98%. The yield of the product was 88% on a purity basis. The resulting 1-aminoanthraquinone contained about 1% of 1,8-diaminoanthraquinone and only traces of other diamino isomers.

When the above procedure was repeated using 0.052 mole of calcium hydroxide or 0.048 mole of barium hydroxide instead of the sodium hydroxide, the same results were obtained.

EXAMPLE 7

A 500 ml. electromagnetically stirred autoclave was charged with 10 g of 1-nitroanthraquinone having a purity of 91.5% and containing 7.0% of 1,5-dinitroanthraquinone, 0.5% of 1,8-dinitroanthroquinone and 1.0% of anthraquinone as impurities, 120 g of a 3% aqueous solution of sodium hydroxide (0.01 mole as sodium hydroxide), 80 g of methanol, and 200 mg of 5% palladium-carbon (2% based on the 1-nitroanthraquinone). The 1-nitroanthraquinone was hydrogenated at a temperature of 50° C. and a pressure of 40 to 30 Kg/cm².G. In 60 minutes, 0.16 mole of hydrogen was absorbed, whereupon the reaction was stopped. The inside of the autoclave was purged with nitrogen, and 80 g of a 3% aqueous solution of sodium hydroxide was added. Methanol was distilled off at reduced pressure (60 to 70 mmHg abs.) and 40 to 50° C. Then, the reaction mixture was suction-filtered in a stream of nitrogen to remove the catalyst and the diaminoanthraquinones. The filtrate was oxidized with air at 20 to 30° C. for 2 hours with stirring to afford 7.65 g of 1-aminoanthraquinone having a purity of 98% in a yield of 93% of theory.

EXAMPLE 8

Hydrogenation was carried out in the same way as in Example 7 except that cyclohexane was used instead of the methanol. A predetermined amount of hydrogen was absorbed over the course of 150 minutes, and the inside of the autoclave was purged with nitrogen. The reaction mixture was suction filtered in an atmosphere of nitrogen to separate the catalyst and diaminoanthraquinones. The filtrate was allowed to stand to separate it into two phases. The lower alkaline aqueous phase was oxidized with air at 20° to 30° C. for 2 hours with stirring to afford 7.72 g of 1-aminoanthraquinone having a purity of 98% in a yield of 94% of theory.

EXAMPLE 9

A 1-liter electromagnetically stirred cylindrical glas reactor was charged with 5 g of crude 1 -aminoanthraquinone having a purity of 92% and containing 5% of 1,5-diaminoanthraquinone and 2% of 1,8-diaminoanthraquinone as impurities (0.0206 mole of 1-aminoanthraquinone), 100 g of a 4% aqueous solution of sodium hydroxide (0.1 mole as sodium hydroxide) and 0.1 g of 5% palladium-carbon. The inside of the reactor was purged with hydrogen, and with stirring at 30° C., the crude 1-aminoanthraquinone was hydrogenated. When 0.22 mole of hydrogen was absorbed over the course of 2 hours, the reaction was stopped, and the catalyst and insoluble materials were separated by filtration. The filtrate was oxidized with air at 20° to 30° C. for 1 hour with stirring. The crystals obtained were filtered, washed with water, and dried to afford 4.4 g of 1-aminoanthraquinone. The product had a purity of 99% as determined by an infrared absorption spectroscopic method, and was found to contain 0.2% of 1,8-diaminoanthraquinone as a result of a thin-layer chromatographic analysis. The yield of the product was 94.7% on a purity basis.

When the above procedure was repeated using an aqueous solution containing 0.1 mole of potassium hydroxide, 0.052 mole of calcium hydroxide, or 0.048 mole of barium hydroxide instead of the aqueous solution of sodium hydroxide, the same results were obtained.

EXAMPLE 10

A 500 ml. electromagnetically stirred autoclave was charged with 5 g of crude 1-aminoanthraquinone (having a purity of 92% and containing 5% of 1,5-daminoanthraquinone and 2% of 1,8-diaminoanthraquinone), 100 g of a 4% aqueous solution of sodium hydroxide and 0.5 g of Raney nickel. At room temperature and a pressure of 3 to 5Kg/cm$^2$.G, the crude 1-aminoanthraquinone was hydrogenated with stirring. When 0.021 mole of hydrogen was absorbed, the reaction was stopped, and the catalyst and insoluble materials were removed. The residue was oxidized with air at 20° to 30° C. for 2 hours with stirring to afford 4.6 g of 1-aminoanthraquinone. The product had a purity of 97%, and contained 1% of 1,5-diaminoanthraquinone and 1% of 1,8-diaminoanthraquinone. The yield of the product was 97% on a purity basis.

When the above procedure was repeated except that a 30 % aqueous solution of hydrogen peroxide, a 15% aqueous solution of sodium hypochlorite, or sodium perborate was used instead of the air in the oxidation process, the same results were obtained.

EXAMPLE 11

A 1-liter electromagnetically stirred cylindrical glass reactor was charged with 5.0 g of crude 1-nitroanthraquinone having a purity of 81% and containing 8% of 1,5-dinitroanthraquinone, 4% of 1,8-dinitroanthraquinone and 7% of other dinitroanthraquinones as impurities (0.016 mole of 1-nitroanthraquinone), 100 g of a 4% aqueous solution of sodium hydroxide and 4.2 g (0.067 mole) of 80% hydrated hydrazine. The mixture was stirred at 80° to 100° C. for 3 hours to form a slurry of 1-aminoanthraquinone. The slurry was cooled to room temperature, and 0.1 g of 5% palladium-carbon was added. The inside of the reactor was purged with hydrogen, and the crude 1-nitroanthraquinone was hydrogenated at room temperature. The reaction was stopped when 0.016 mole of hydrogen was absorbed. The catalyst and insoluble materials were separated by filtration. The filtrate was oxidized with air at 20° to 30° C. for 2 hours with stirring to afford 3.2 g of 1-aminoanthraquinone having a purity of 98% and containing 1% of 1,8-diaminoanthraquinone and only traces of other diaminoanthraquinones as impurities. The yield of 1-aminoanthraquinone was 88% on a purity basis.

EXAMPLE 12

A 500 ml. of electromagnetically stirred autoclave was charged with 5 g of crude 1-aminoanthraquinone having a purity of 92% and containing 5% of 1,5-diaminoanthraquinone and 2% of 1,8-diaminoanthraquinone, 60 g of a 3% aqueous solution of sodium hydroxide, 40 g of methanol and 0.05 g of 5% pallidium-carbon, and the crude 1-aminoanthraquinone was hydrogenated with stirring at a temperature of 50° C. and a pressure of 40 to 30 Kg/cm$^2$.G. The reaction proceeded smoothly. When 0.0196 mole of hydrogen was absorbed, the reaction was stopped. The inside of the autoclave was purged with nitrogen, and 40 g of a 3% aqueous solution of sodium hydroxide was added. Methanol was distilled off at reduced pressure (60 to 70 mmHg abs.) and a temperature of 40° to 50° C. The reaction mixture was suction filtered in an atmosphere of nitrogen to remove the catalyst and diaminoanthraquinones. The filtrate was oxidized with air at 20° to 30°C. for 2 hours with stirring to afford 4.4 g of 1-aminoanthraquinone having a purity of 98% in a yield of 94%.

EXAMPLE 13

A predetermined amount of hydrogen was absorbed by operating in the same way as in Example 12 except that cyclohexane was used instead of methanol. The inside of the autoclave was purged with nitrogen, and the reaction mixture was filtered in an atmosphere of nitrogen to separate the catalyst and diaminoanthraquinones. The filtrate was allowed to stand to separate into two phases. The lower aqueous phase was oxidized with air at 20° to 30° C. for 2 hours to afford 1-aminoanthraquinone having a purity of 98% in a yield of 94%.

What we claim is:

1. A process for preparing 1-aminoanthraquinone of high purity, which comprises hydrogenating 1-nitroanthraquinone or crude 1-aminoanthraquinone in an aqueous medium in the presence of a base using a hydrogenating catalyst thereby forming an hydrogenation product which comprises a water soluble salt of 1-aminoanthrahydroquinone and said base, and the oxidizing the hydrogenation product.

2. The process of claim 1 wherein the aqueous medium is water.

3. The process of claim 1 wherein the aqueous medium is a mixture of water and an organic solvent, the latter being contained in a proportion of not more than 40 % by weight of the mixture.

4. The process of claim 3 wherein the organic solvent is selected from the group consisting of aromatic hydrocarbons substituted by one to several halogen atoms, aliphatic, araliphatic and cycloaliphatic hydrocarbons containing 5 to 12 carbon atoms, halogenated aliphatic hydrocarbons substituted by one to several halogen atoms and containing 1 to 6 carbon atoms, ethers selected from anisole, dialkyl ethers, tetrahydrofuran and dioxane, aliphatic and cycloaliphatic ketones selected from acetone, methyl ethyl ketone and cyclohexanone, and monohydric or polyhydric aliphatic and cycloaliphatic alcohols containing 1 to 6 carbon atoms.

5. The process of claim 1 wherein an alkali metal or alkaline earth metal hydroxide is added as the base at the outset of, or during, the hydrogenation in an amount of at least 2/$n$ per mole of the starting material in which $n$ is the atomic valency of the alkali metal or alkaline earth metal.

6. The process of claim 1 wherein the base is an hydroxide, oxide, carbonate, acetate or phosphate of an alkali metal or alkaline earth metal, ammonia, diethylamine, morpholine, piperidine, ethanolamine, piperazine, ethylenediamine, 1,4-diazabicyclooctane or 1,7-diazaundecene.

7. The process of claim 1 which comprises hydrogenating 1-nitroanthraquinone in an aqueous medium in the presence of a base using a hydrogenating catalyst, then oxidizing the hydrogenation product, filtering it to withdraw a mixture of 1-aminoanthraquinone and the hydrogenating catalyst, dissolving the 1-aminoanthraquinone of said mixture in an aliphatic glycol, alicyclic alcohol, carboxylic acid amide, ether, substituted aromatic hydrocarbon, ether alcohol, sulfuric acid or dimethyl sulfoxide, and cooling, diluting with water or concentrating the 1-aminoanthraquinone solution separated from the hydrogenation catalyst by filtration, thereby to precipitate and withdraw the 1-aminoanthraquinone.

8. The process of claim 1 which comprises effecting the hydrogenation with the addition of an alkali metal or alkaline earth metal as the base at the outset of or during the hydrogenation in an amount of at least $2/n$ moles per mole of 1-nitroanthraquinone in which $n$ is the atomic valency of the alkali metal or alkaline earth metal, after the hydrogenation completes, separating the hydrogenatin catalyst by filtration, and oxidizing the filtrate, thereby to precipitate and withdraw the 1-aminoanthraquinone.

9. The process of claim 1 which comprises hydrogenating crude 1-nitroanthraquinone containing dinitroanthraquinones as impurities or crude 1-aminoanthraquinone containing diaminoanthraquinones as impurities in an aqueous medium in the presence of a base using a hydrogenating catalyst, stopping the hydrogenation at a time when the 1-nitroanthraquinone or 1-aminoanthraquinone has been substantially reduced to 1-aminoanthrahydroquinone but the dinitroanthraquinones or diaminoanthraquinones remain substantially unreduced to diaminoanthrahydroquinones, removing water-insoluble materials from the reaction mixture, and then oxidizing the remaining water-soluble residue.

10. The process of claim 9 wherein the aqueous medium is water.

11. The process of claim 9 wherein the aqueous medium is a mixture of water and an organic solvent, the latter being contained in a proportion of not more than 40% by weight of the mixture.

12. The process of claim 11 wherein the organic solvent is selected from the group consisting of aromatic hydrocarbons substituted by one to several halogen atoms, aliphatic, araliphatic and cycloaliphatic hydrocarbons containing 5 to 12 carbon atoms, halogenated aliphatic hydrocarbons substituted by one to several halogen atoms and containig 1 to 6 carbon atoms, ether selected from anisole, dialkyl ethers, tetrahydrofuran and dioxane, aliphatic and cycloaliphatic ketons selected from acetone, methyl ethyl ketone and cyclohexanone, and monohydric or polyhydrric aliphatic and cycloaliphatic alcohols containing to 6 carbon atoms.

13. The process of claim 9 wherein an alkali metal or alkaline earth metal hydroxide is added as the base at the outset of, or during, the hydrogenation in an amount of at least $2n$ moles per mole of the starting material in which $n$ is the atomic valency of the alkali metal or alkaline earth metal.

14. The process of claim 9 wherein the base is an hydroxide, oxide, carbonate, acetate or phosphate of an alkali metal or alkaline earth metal, ammonia, diethylamine, morpholine, piperidine, ethanolamine, piperazine, ethylenediamine, 1,4-diazabicyclooctane or 1,7-diazaundecene.

* * * * *